United States Patent
Castagner et al.

(10) Patent No.: US 9,751,903 B2
(45) Date of Patent: Sep. 5, 2017

(54) PHARMACEUTICAL COMPOUNDS FOR USE IN THE THERAPY OF CLOSTRIDIUM DIFFICILE INFECTION

(71) Applicant: ETH Zurich, Zurich (CH)

(72) Inventors: Bastien Castagner, Zurich (CH);
Jean-Christophe Leroux, Zurich (CH);
Mattias Ivarsson, Zurich (CH);
Gisbert Schneider, Zurich (CH); Anna Pratsinis, Zurich (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 15/172,171

(22) Filed: Jun. 3, 2016

(65) Prior Publication Data

US 2016/0280727 A1   Sep. 29, 2016

Related U.S. Application Data

(63) Continuation-in-part of application No. 14/347,649, filed as application No. PCT/EP2012/004088 on Sep. 28, 2012, now Pat. No. 9,358,243.

(30) Foreign Application Priority Data

Sep. 29, 2011  (EP) .................................... 11007933
Sep. 29, 2011  (EP) .................................... 11007935

(51) Int. Cl.
C07F 9/117   (2006.01)
A61K 31/6615   (2006.01)

(52) U.S. Cl.
CPC .................................. *C07F 9/117* (2013.01)

(58) Field of Classification Search
CPC ...................................................... C07F 9/117
See application file for complete search history.

(56) References Cited

U.S. PATENT DOCUMENTS 5,278,332 A       1/1994  Siren
2010/0048730 A1  2/2010  Li et al.
2012/0258936 A1  10/2012 Savidge

FOREIGN PATENT DOCUMENTS

JP  54044901 A   *  4/1979
JP  S54-044901         4/1979
WO  WO 2010/049921    5/2010
WO  WO 2012/138963   10/2012

OTHER PUBLICATIONS

CAS Registry No. 1428567-01-4 [Entered STN: Apr. 17, 2013].*

(Continued)

*Primary Examiner* — Michael Barker
*Assistant Examiner* — Amanda L Aguirre
(74) *Attorney, Agent, or Firm* — JMB Davis Ben-David (57) ABSTRACT

The invention relates to a compound described by a general formula (1), wherein each X independently from other X can be $OPO_3^{2-}$, $OPSO_2^{2-}$ or $OSO_3^-$; $R^1$ is a solubility function such as a polyethylene glycol moiety. The invention further relates to the use of the compounds according to the invention in the therapy of infection by *Clostridium difficile*.

19 Claims, 8 Drawing Sheets

(56) References Cited

OTHER PUBLICATIONS

English machine translation of JP 54044901A obtained Jun. 9, 2017.*
Partial Translation of JP 54044901A, Irina Knizhnik, USPTO Alexandria, VA (Jan. 2017).*
STN CAplus entry for JP 54044901A (1979).*
G. Guttenberg et al., "Inositol Hexakisphosphate-dependent Processing of Clostridium Sordellii Lethal Toxin and Clostridium novyi—Toxin", Journal of Biological Chemistry, vol. 286, No. 17, Apr. 29, 2011, p. 14779-4786.
Florin I et. al. "Polyphosphate-mediated protection from cellular intoxication with Clostridium difficile toxin B", Biochimica ET Biophysica Acta, Molecular Cell Research, Elsevier Science Publshers, Amsterday, NL, vol. 805, No. 2, Oct. 12, 1984, pp. 131-136.
Xu et al. "Synthesis of phosphatase-resistant analogues of phytic acid (InsP6)" Tetrahedron Lett. 2005, 46, 8311-8314.

* cited by examiner

PHARMACEUTICAL COMPOUNDS FOR USE IN THE THERAPY OF CLOSTRIDIUM DIFFICILE INFECTION

CROSS REFERENCE TO RELATED APPLICATIONS

This is a Continuation-in-Part of co-pending U.S. patent application Ser. No. 14/347,649, filed Mar. 27, 2014, which is the U.S. National Stage of International Application No. PCT/EP2012/004088, filed Sep. 28, 2012, which in turn claimed the benefit of European Patent Application No. 11007935.7, filed Sep. 29, 2011 and European Patent Application No. 11007933.2, filed Sep. 29, 2011. The foregoing applications are incorporated by reference in their entirety herein.

FIELD

The present invention relates to enteric activators of *Clostridium difficile* toxin, particularly poly-phosphate derivatives, polysulfate derivatives or mixed polyphosphate/sulphate derivatives of six-membered cyclic polyols comprising a polyethylene glycol (PEG) moiety.

BACKGROUND

*Clostridium difficile* is a species of Gram-positive bacteria that causes severe diarrhoea in human patients. *C. difficile* infection (CDI) typically affects patients under antibiotic treatment since the bacterium is only able to colonize the colon of patients with depleted bacterial flora. The emergence of antibiotic-resistant strains of *C. difficile* causes increasingly severe morbidity and mortality due to the spread of new, more virulent strains, with recent outbreaks in North America and Europe.

*C. difficile* asymptomatically colonizes 2-5% of the human adult population. The bacteria form spores, which are difficult to neutralize by common methods of disinfection. As a result, *C. difficile* infections are a common result of prolonged stays in hospitals; the pathogen is considered the leading cause of hospital-associated diarrhoea in the USA.

Current therapy of choice is oral application of metronidazole or, in case of failure of the former, vancomycin. Since clinical symptoms of CDI are caused by two toxic proteins secreted by *C. difficile* in the colon, rather than by the presence of the bacteria itself, efforts have been made recently to target these toxins (e.g. employing polymeric binders), but have so far failed in clinical trials.

*C. difficile* enterotoxin (toxin A, TcdA) and cytotoxin (toxin B, TcdB) are the main contributors to the symptoms of disease (for a toxin biology review, see Voth and Ballard, *Clinical Microbiology Reviews* 2005, 18, 247-263). In brief, both toxins are composed of four domains, a first domain mediating the attachment of the toxin to cells; a second one facilitating translocation into the cytosol; a third domain causing the cleavage of the toxic domain by autoproteolysis, and finally the toxic domain or "warhead" itself, which causes the physiological effects of the toxin in the affected cell.

Reineke et al. (*Nature* 2007, 446, 415) identified myo-inositol hexakisphosphate (IP6) as the natural trigger of TcdA/TcdB autoprocessing in the cell cytosol. Egerer et al. (*PLoS Pathog.* 2010, 6, e1000942) and Shen et al. (*Nat. Struct. Mol. Biol.* 2011, 18, 364) suggested targeting the IP6-induced autoprocessing mechanism as a means of therapeutic intervention against toxin-mediated pathogenicity.

Kreimeyer et al. suggested using IP6 pharmaceutically to intervene in CDI (*Naunyn-Schmiedeberg's Arch. Pharmacol.* 2011, 383, 253). However, this approach is not feasible as the presence of high calcium concentrations in the colon precipitates IP6 and prevents it from being active.

Thus, the objective of the present invention is to provide improved treatment options for patients suffering from CDI. This objective is attained by the subject-matter of the independent claims.

SUMMARY AND DETAILED DESCRIPTION

The invention is based on a novel design of small-molecule analogues of IP6 that are provided as an oral therapy to trigger the cleavage of the toxin in the colon lumen, thereby detaching the toxin warhead before it reaches its destination, and rendering it harmless. IP6 itself cannot be used for this purpose because it is not soluble at the high calcium concentrations found in the colon lumen. The present invention provides novel IP6 analogues with improved solubility.

According to a first aspect of the invention, a pharmaceutical compound characterized by a general formula (1) is provided, $$\text{(1)}$$

wherein
- $R^1$ is or comprises a solubility function $R^2$ selected from the group including
  - a polyethylene glycol and
  - a polyglycerol, for example a polyglycerol described by the formula $R^3$—O—$(CH_2$—CHOH—$CH_2O)_n$— wherein $R^3$ is hydrogen, methyl or ethyl, and n has a value from 3 to 200, or a branched or hyperbranched polyglycerol, such as may be described by the formula R³—O—(CH₂—CHOR⁵—CH₂—O)ₙ—, wherein R⁵ is hydrogen or a glycerol chain and R³ is hydrogen, methyl or ethyl;

and each X independently of any other X is selected from $OPO_3^{2-}$, $OPSO_2^{2-}$, or $OSO_3^-$.

In certain embodiments, $R^1$ is a polyethylene glycol.

In certain embodiments, $R^1$ is a polyethylene glycol described by a formula (R³—(O—OCH₂—CH₂)ₙ—) and R³ is hydrogen, methyl or ethyl, and n has a value from 2 to 200.

In certain embodiments, n has a value from 3 to 200.

In certain embodiments, n has a value from 3 to 20. In certain embodiments, n has a value from 10 to 30. In certain embodiments, n has a value from 9 to 45.

In certain embodiments, n has a value from 7 to 11.

In certain embodiments, n has a value of 2. In certain embodiments, n has a value of 7. In certain embodiments, n has a value of 9. In certain embodiments, n has a value of 11. In certain embodiments, n has a value of 45.

In certain embodiments, said polyethylene glycol is a branched polyethylene glycol.

In certain embodiments, $R^1$ comprises an ether, thioether, carboxylic ester, amine, carboxylic amide, urea, sulfonamide, phosphoramide, phosphate ester, phosphorothioate, alkyl, triazole or carbamate function, or a combination of any of the preceding groups, which links $R^2$ to the molecule.

In certain embodiments, $R^1$ is a CH₂ or a CH₂CH₂ group linking $R^2$ to the molecule.

Formula (1) describes a six-membered alkyl ring and $R^1$ is covalently attached to one of the carbon atoms (a CH moiety) forming the ring.

In certain embodiments, $R^2$ is a polyglycerol described by the formula ((R³—O—(CH₂—CHOH—CH₂O)ₙ—) with R³ being hydrogen, methyl or ethyl, and n having a value from 3 to 200. In some alternatives of these embodiments, n has a value from 3 to 20. In some alternatives of these embodiments, n has a value from 10 to 30. In some alternatives of these embodiments, n has a value from 9 to 45.

In certain embodiments, $R^2$ is a branched polyglycerol described by the formula (R³—O—(CH₂—CHOR⁵—CH₂—O)ₙ—) with R⁵ being hydrogen or a linear glycerol chain described by the formula (R³—O—(CH₂—CHOH—CH₂—O)ₙ—) and R³ being hydrogen, methyl or ethyl.

In certain embodiments, $R^2$ is a hyperbranched polyglycerol described by the formula (R³—O—(CH₂—CHOR⁵—CH₂—O)ₙ—) with R⁵ being hydrogen or a glycerol chain described by the formula (R³—O—(CH₂—CHOR⁶—CH₂—O)ₙ—), with R⁶ being hydrogen or a glycerol chain described by the formula (R³—O—(CH₂—CHOR⁷—CH₂—O)ₙ—), with R⁷ being hydrogen or a linear glycerol chain described by the formula (R³—O—(CH₂—CHOH—CH₂—O)ₙ—) and R³ being hydrogen, methyl or ethyl.

Hyperbranched glycerol and methods for its synthesis are described in Oudshorn et al., Biomaterials (2006), 27, 5471-5479; Wilms et al., Acc. Chem. Res. (2010) 43, 129-41, and references cited therein.

In embodiments wherein the solubility function is attached to the compound directly, $R^1$ equals (is) $R^2$.

The solubility function provides for the solubility of the molecule in aqueous solution in the presence of 10 mmol/l $Ca^{2+}$. The molecule according to the invention has a higher solubility than IP6 in concentrations of calcium higher than 1 mmol/l. In certain embodiments, the solubility of the molecule of the invention is above 10 μmol/l.

The compound of the invention comprises a six-membered ring, wherein ring members can be described by a formula CH—X, and one ring member can be described by a formula CH—R¹, wherein each X (independently of any other X) and $R^1$ have the meaning defined above.

In certain embodiments, the compound according to the invention is characterized by a general formula (2a) or (3a)

(2a)

(3a)

wherein each X (independently) and $R^1$ have the meaning outlined above.

In certain embodiments, the compound according to the invention is characterized by a general formula (2b) or (3b)

(2b)

(3b)

wherein each X (independently) and $R^1$ have the meaning outlined above.

In certain embodiments, the compound of the invention is described by a formula (1). In certain embodiments, it is described by formulae (2a) or (2b). In certain embodiments, it is described by formulae (3a) or (3b).

In certain embodiments, the compound is described by a general formula (4a) or (4b)

(4a)

(4b)

wherein R¹ has the same meaning as indicated above.

In one embodiment, (4a) comprises a poly(ethylene glycol) $PEG_{400}$ as solubility function, with R¹ being $CH_3(OCH_2—CH_2)_9—O—$:

(7)

myo-inositol-pentakisphosphate-2-PEG(400) (7) is the $PEG_{400}$-analogue of myo-inositol hexakisphosphate. (7) has proved to have an improved ability to cleave TcdB CPD in the presence of calcium.

Another embodiment relates to the $PEG_{2000}$ analogue to (7), i.e. a PEG with approximately 45 ethylene glycol monomers.

Another embodiment relates to the $PEG_{100}$ analogue to (7), i.e. a PEG with 2 ethylene glycol monomers.

Another embodiment relates to the $PEG_{320}$ analogue to (7), i.e. a PEG with 7 ethylene glycol monomers.

Another embodiment relates to the $PEG_{500}$ analogue to (7), i.e. a PEG with 11 ethylene glycol monomers.

Another embodiment relates to an analogue to scyllo-inositol hexakisphosphate as described by formula (4b)

(4b)

wherein $R^1$ has the same meaning as outlined above. In some embodiments, the compound of the invention can be described by formula (4b) and $R^1$ is a poly(ethylene glycol) moiety.

In certain embodiments, the compound is described by a general formula (5a) or (5b)

(5a)

-continued (5b)

wherein $R^1$ has the same meaning as indicated above.

In certain embodiments, the compound is described by a general formula (6a) or (6b)

(6a)

(6b)

wherein $R^1$ has the same meaning as indicated above.

In certain embodiments, the polyethylene glycol is $CH_3(OCH_2—CH_2)_9—O—$ or $CH_3(OCH_2—CH_2)_{45}—O—$.

In certain embodiments, the polyethylene glycol is $CH_3(OCH_2—CH_2)_2—O—$, $CH_3(OCH_2—CH_2)_7—O—$ or $CH_3(OCH_2—CH_2)_{11}—O—$.

In certain embodiments, the polyethylene glycol is a monodisperse polyethylene glycol. In the context of the present specification, the term "monodisperse polyethylene glycol", abbreviated also as "mdPEG", refers to a polyethylene glycol (PEG) moiety that has a single, defined chain length and molecular weight. mdPEGs are typically generated by separation of individual chain length polymer species from the polymerization mixture by chromatography.

In certain embodiments, the compound is described by any one of formulae (7) to (13)

(7)

(8)

(9)

-continued

(10)

(11)

(12)

(13)

The solubility function, a poly(ethylene glycol) (PEG) chain shown here as a non-limiting example, is attached to the molecule to render it soluble in the colon lumen, at the concentrations of calcium present therein.

The compounds defined above can be synthesized according to standard methods. The synthesis of compounds (5a) and (6a) is described in the examples of the present invention.

According to another aspect of the invention, a compound according to any of the above aspects of the invention, in the broadest definition given, or as specified in any of the embodiments, is provided for use as a medicament. In particular examples of such embodiments, the medicament can contain pharmaceutically-acceptable carriers, salts, and/or excipients as known to the art.

According to yet another aspect of the invention, a compound according to any of the above aspects of the invention, in the broadest definition given, or as specified in any of the embodiments, is provided for use in methods for treatment or prevention of C. difficile infection. In such methods, the compound described herein (including a dosage form or formulation as described), is administered to a subject in need thereof, thereby treating or preventing the C. difficile infection. In particular embodiments, the methods include administration of additional antibiotic agents, in addition to the described compound, or as part of a combined treatment or dosage form, as described herein.

A compound according to the invention may be given to a patient already diagnosed with CDI, or to a patient being suspected of suffering from CDI. Alternatively, the compound may be used as a prophylactic for patients that are at risk of contracting the infection, such as patients under antibiotic treatment in hospital settings. The compounds according to the invention are simple to synthesize, resistant to degradation in the gastro-intestinal tract and unlikely to be absorbed into the bloodstream, thus avoiding potential side effects. The compounds according to the invention do not need to penetrate mammalian or bacterial membranes to be active, which makes them more effective in vivo. In addition, the compounds according to the invention are unlikely to exert selective pressure on the bacteria and therefore avoid problems related to resistance.

According to yet another aspect of the invention, a pharmaceutical composition for use in a method for the prevention or treatment of C. difficile infection is provided, comprising a compound according to any of the above aspects of the invention.

Particular pharmaceutical compositions comprise from approximately 1% to approximately 95% active ingredient, preferably from approximately 20% to approximately 90% active ingredient.

A pharmaceutical composition according to the above aspects of the invention can be administered alone or in combination with one or more other therapeutic agents. A combination therapy may take the form of fixed combinations of the compound of the invention and one or more other antibiotic agents. Administration may be staggered; alternatively drugs may be given independently of one another, or as a fixed combination.

According to a particular embodiment, a pharmaceutical composition comprises a compound of the invention according to any of the above aspects of the invention, and additionally metronidazole, vancomycin and/or fidaxomicin.

According to yet another aspect of the invention, a dosage form is provided comprising a compound according to any of the above aspects of the invention. A peroral formulation, particularly a tablet, syrup, solution, capsule or powder is preferred.

According to a particular embodiment, such a dosage form additionally comprises an antibiotically active compound, such as (by way of non-limiting example) metronidazole, vancomycin or fidaxomicin.

According to yet another aspect of the invention a treatment regime is provided for the prevention and treatment of CDI, comprising the administration of a compound according to the invention. Administration may be effected by any of the means described herein.

Also within the scope of the present invention is a method for the prevention or treatment of CDI, comprising the administration a compound according to the invention to a subject in need thereof.

The compound according to the invention can also be used in the therapy or prevention of conditions related to pathological calcium crystallization.

Physiological calcium and phosphate concentrations in the blood are close to supersaturation. Blood components such as fetuin-A interact with calcium and phosphate to form soluble nanoparticles termed calciprotein particles (CPPs) that prevent precipitation and resultant calcification under normal conditions. So-called primary CPPs are amorphous and have a hydrodynamic radius of typically less than 100 nm and mature with time to reorganize into crystalline secondary CPPs that have a hydrodynamic radius of more than 100 nm. Secondary CPPs are subsequently thought to progress to calcification and to initiate pathological responses.

Pharmaceutical agents capable of reducing the propensity for progression of primary CPPs to secondary CPPs, and hence ultimately capable of reducing pathological crystallization are of significant therapeutic value. The inventors show that the compounds according to the invention are capable of reducing pathological calcium crystallization.

Conditions related to pathological calcium crystallization for which the compounds of the present invention are particularly useful include vascular calcification, coronary artery disease, vascular stiffening, valvular calcification, nephrocalcinosis, calcinosis cutis, kidney stones, chondrocalcinosis, osteoporosis, myocardial infarction, cardiovascular mortality (particularly in chronic kidney disease patients), progression of chronic kidney disease and failure of renal transplant grafts. Pathological crystallization has been shown to be associated with all-cause mortality of chronic kidney disease CKD) patients, hence the compounds of the present invention are indicated for chronic kidney disease patients in general.

Figure 7:
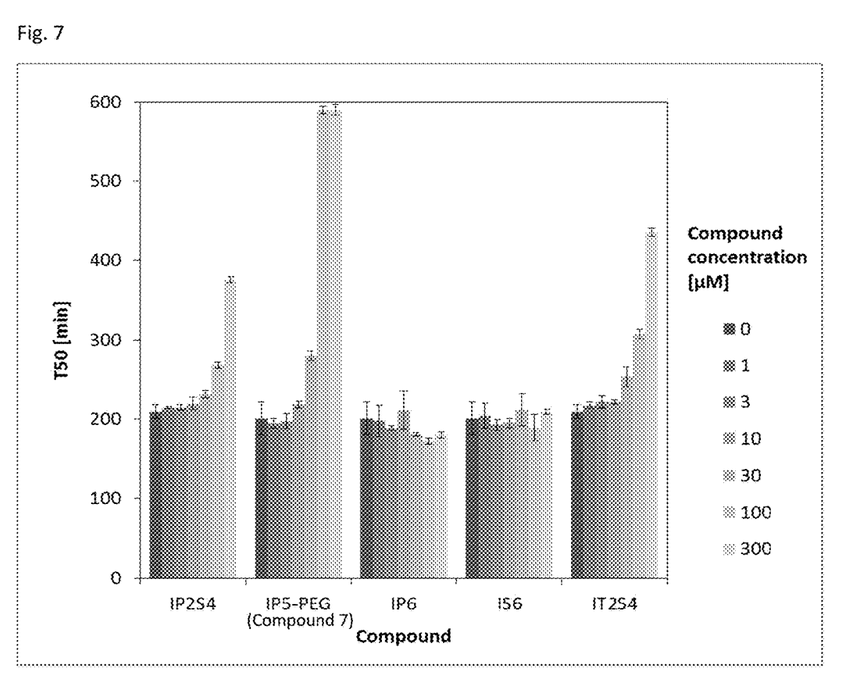
FIG. 7 shows that compound (7) is able to inhibit the transition of primary to secondary CPPs and thus can reduce the propensity for calcification of human serum.

One embodiment of the invention that shows a particularly high activity is the use of 2-PEG-IP5 (myo-pentakis-inositolphosphate-(2)-PEG) with PEG moieties having a molar mass of approximately 400 g/mol (n=9) or approximately 2000 g/mol (n=45) for the indications listed above. This conclusion is drawn from the results of an in vitro assay that measures the propensity for calcification of human serum, which has been clinically validated as a predictor of all-cause mortality in CKD patients and renal transplant patients (FIG. 7). The inventors show that IP5-PEG is a very potent inhibitor in reducing the propensity for calcification of human serum.

Wherever alternatives for single features such as $R^1$, $R^2$, X etc. are laid out herein as "embodiments", it is to be understood that such alternatives may be combined freely to form discrete embodiments of the entire molecule provided as such or for use in a method or medical indication herein. Thus, any of the alternative embodiments for $R^1$ may be combined with any of the alternative embodiments of X provided in the formulae mentioned herein.

EXAMPLES

1. Synthesis of Compound (7)

Figure 3:
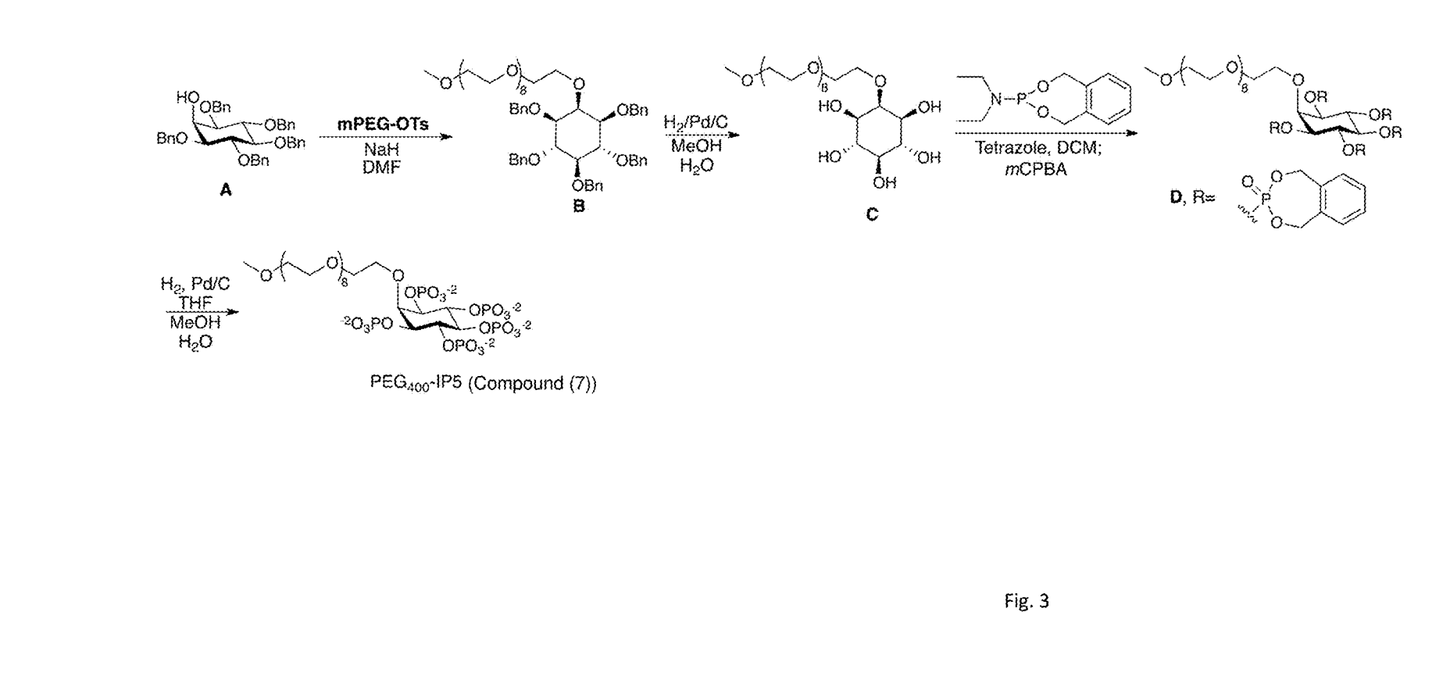
FIG. 3 shows the synthesis of compound (7).
Figure 4:
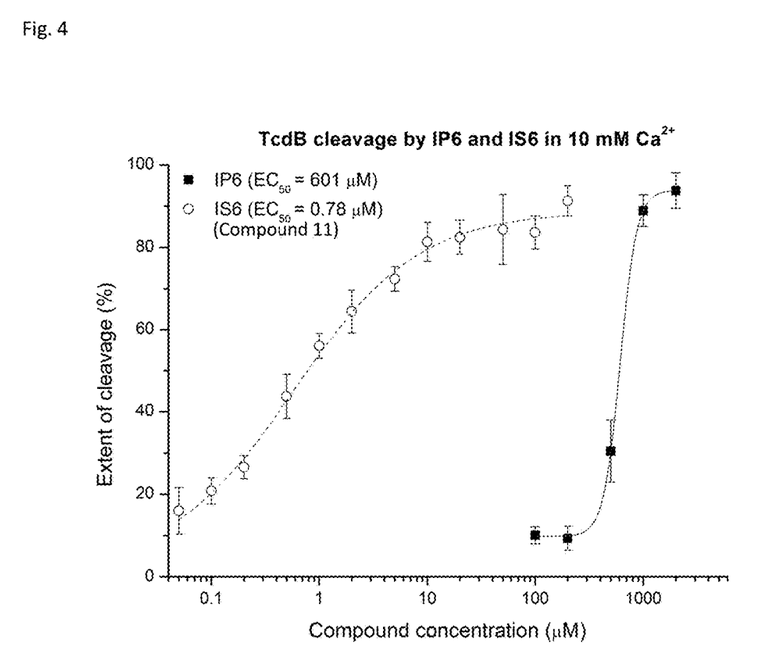
FIG. 4 shows the concentration dependence of cleavage of TcdB cysteine protease domain in the presence of 10 mM $Ca^{2+}$ for activator compound (11); activator data shown as empty circles; IP6 control as black squares.

The synthesis followed the sequence depicted in FIG. 3.

Compound B: To a suspension of sodium hydride (4.3 mmol, 103.7 mg) in 10 mL dimethylformamide (DMF) was added a solution of compound A [Martin, S. F. et al., *J. Org. Chem.* 1994, 59, 4805] (2.16 mmol, 1363 mg) in DMF (10 mL) dropwise. When the addition was complete the mixture was stirred for 30 min at room temperature, followed by addition of MeO-PEG-OTs (OTs being toluenesulfonate) (3.2 mmol, 1.64 g in 10 mL DMF). The reaction was allowed to stir overnight, then quenched with water (5 mL). The mixture was extracted with dichloromethane (DCM). The solvent was evaporated and the residue was chromatographed on silica gel with six 100 mL portions of 20:80; 30:70; 40:60; 60:40; 80:20; 100:0 of ethylacetate:hexanes. The chromatography resulted in the fractionation of product with different PEG sizes, including compound B with an average of 9 PEG units. $^1$H NMR (400 MHz; CDCl$_3$): δ 7.29-7.13 (m, 25H), 4.83 (d, J=10.8 Hz, 2H), 4.79 (s, 2H), 4.74 (d, J=10.8 Hz, 2H), 4.63 (d, J=11.7 Hz, 2H), 4.59 (d, J=11.6 Hz, 2H), 3.97-3.88 (m, 5H), 3.64-3.42 (m, 31H), 3.38 (t, J=9.2 Hz, 1H), 3.29-3.25 (m, 5H).

Compound C: Compound B was dissolved in a mixture of tetrahydrofuran (THF, 4 mL), methanol (7 mL) and water (3 mL), followed by addition of excess 10% palladium on charcoal. The mixture was placed under a hydrogen atmosphere and stirred overnight at room temperature. The reaction mixture was then purged with nitrogen, filtered and the solvent evaporated. The crude mixture was purified on a reverse phase cartridge (Sep-Pak, Waters, 1 g, C$_{18}$, Cat.# WAT 036905) by eluting with 10 mL water. All fractions (1.5 ml) were lyophilized and analyzed by $^1$H NMR analysis. $^1$H NMR (400 MHz; D$_2$O): δ 3.96-3.94 (m, 2H), 3.89 (t, J=2.8 Hz, 1H), 3.78-3.69 (m, 28H), 3.69-3.60 (m, 5H), 3.56 (dd, J=10.0, 2.8 Hz, 2H), 3.40 (s, 3H), 3.25 (t, J=9.2 Hz, 1H).

Compound D: Compound C (0.2 mmol, 119 mg) was suspended in tetrazole (3.630 mmol, 8.1 mL, 0.45 M in CH$_3$CN) and DCM (10 mL) then N,N-diethyl-1,5-dihydro-2,4,3-benzodioxaphosphepin-3-amine (1.8 mmol, 434 mg) was added and the mixture was stirred at room temperature overnight. The mixture was then cooled to −10° C. and a solution of meta-chloroperoxybenzoic acid (mCPBA, pre-dried over Na$_2$SO$_4$, 4.8 mmol, 1189 mg) in DCM (2 mL) was added. The mixture was allowed to stir at −10° C. for an additional 10 min, and then it was brought to room temperature and stirred for 1 hour. The mixture was washed with dilute sodium sulfite and extracted with DCM. The organic layers were dried with Na$_2$SO$_4$, filtered and concentrated. The residue was chromatographed on silica gel with a gradient of 1-5% methanol in DCM. $^1$H NMR (400 MHz; CDCl$_3$): δ 7.41-7.27 (m, 18H), 7.21 (dd, J=6.9, 1.7 Hz, 2H), 5.59-5.51 (m, 6H), 5.44 (t, J=14.2 Hz, 2H), 5.37-5.29 (m, 6H), 5.25-4.95 (m, 10H), 4.74 (ddd, J=9.9, 7.6, 2.1 Hz, 2H), 4.61 (t, J=2.2 Hz, 1H), 4.03 (t, J=4.9 Hz, 2H), 3.68-3.50 (m, 22H), 3.48 (dd, J=6.1, 4.0 Hz, 2H), 3.40-3.34 (m, 7H). $^{13}$C NMR (101 MHz; CDCl$_3$): δ 135.78, 135.72, 135.4, 135.14, 134.99, 129.38, 129.27, 129.26, 129.22, 129.14, 129.11, 128.96, 128.95, 77.6, 76.05, 76.01, 73.8, 71.9, 70.67, 70.60, 70.57, 70.54, 70.53, 70.49, 70.38, 70.34, 70.29, 69.46, 69.39, 69.33, 69.24, 69.16, 69.01, 68.95, 59.0

Compound (7): Compound D was dissolved in a mixture of THF (1 mL), methanol (1.5 mL) and water (2 mL), followed by addition of excess 10% palladium on charcoal. the mixture was placed under an hydrogen atmosphere and stirred overnight at room temperature. The mixture was then purged with nitrogen, filtered and concentrated. The compound was brought at pH 7 by addition of dilute aqueous NaOH (170 µl, 0.1M). The residue was purified on a sephadex column (PD-10, GE Healthcare, Sephadex G-25 M, cat.#17-0851-01) by eluting with 10 ml of water. All fractions (1.5 mL) were lyophilized and analyzed by $^1$H NMR. The fractions containing product were purified further on a reverse phase cartridge (Sep-Pak, Waters, 1 g, C$_{18}$, cat.# WAT 036905) by eluting with 10 mL water. All fractions (1.5 ml) were lyophilized and analyzed by $^1$H NMR analysis. $^1$H NMR (400 MHz; D$_2$O): δ 4.44 (q, J=9.4 Hz, 2H), 4.20 (s, 1H), 4.16-4.10 (m, 3H), 4.06 (t, J=4.7 Hz, 2H), 3.83-3.63 (m, 26H), 3.40 (s, 3H). $^{31}$P NMR (162 MHz; D$_2$O): δ 1.5, 1.2, 0.8

2. Determination of EC50 in Presence of 10 mM Ca$^{2+}$

The compound to be tested was added to a recombinant His-tagged cysteine protease domain of *C. difficile* toxin B in the presence of 10 mM Ca$^{2+}$ in 100 mM Tris pH7.4 and incubated for 2 h at 37° C. Cleaved protein fragments were separated by SDS-PAGE and visualized by Coomassie staining. The extent of cleavage quantified from protein band intensities using the ImageJ software package. Signals were normalized to cleavage of positive and negative controls.

Figure 1A:
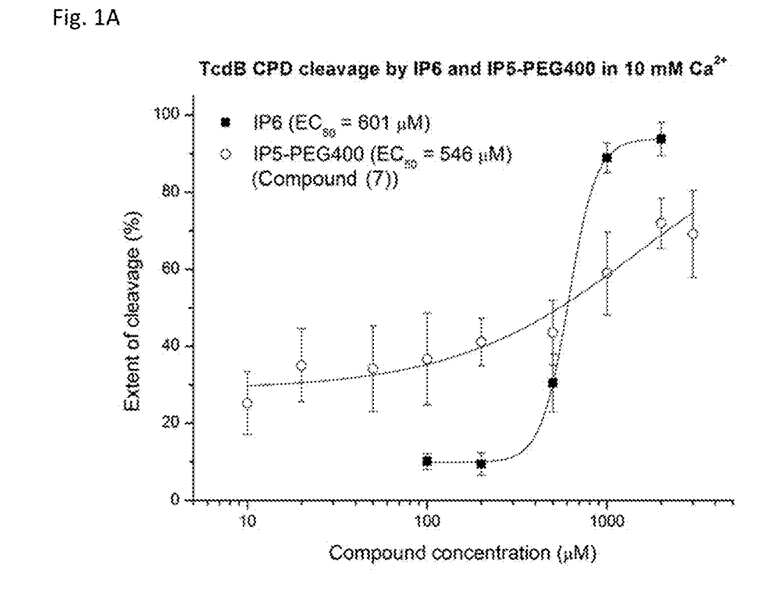
FIGS. 1A and 1B show the concentration dependence of cleavage of TcdB cysteine protease domain in the presence of activator compound (7) (empty circles) or IP6 in vitro (FIG. 1A), and the corresponding kinetics (FIG. 1B) in 10 mM $Ca^{2+}$.

The results of this assay for IP6 and compound (7) are shown in FIG. 1A. These demonstrate that 50% the cleavage of toxin fragment is achieved at similar concentrations of IP6 and (7). The activity of IP6 disappears almost completely at 100 µM whereas (7) retains residual activity. The PEG chain of (7) likely confers the molecule with a wider window of solubility.

3. Comparison of Cleavage Kinetics

Figure 1B:
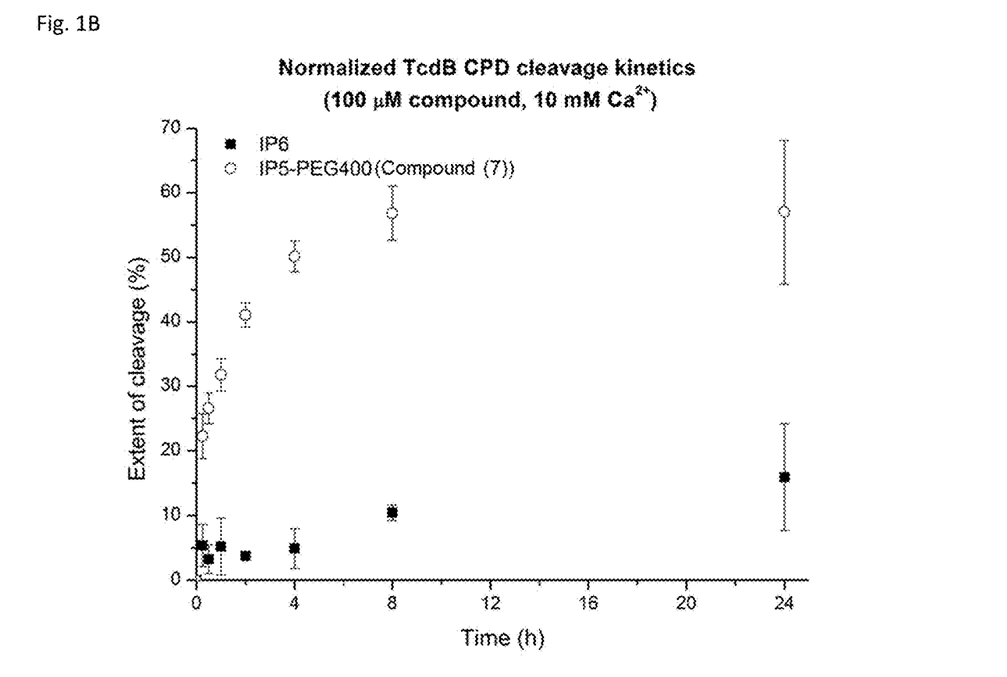
Figure 2:
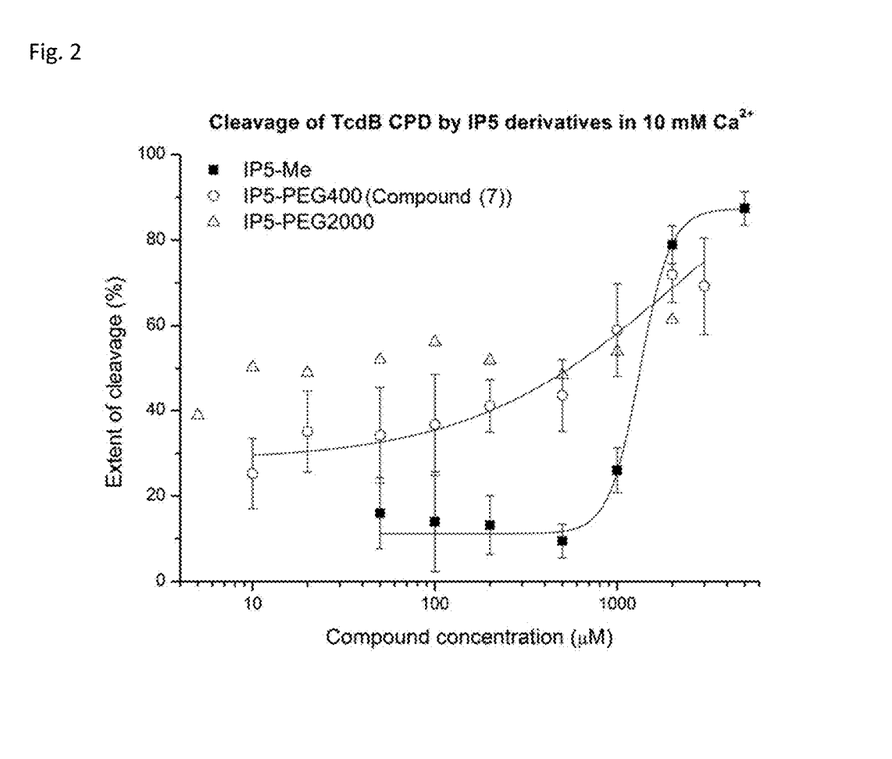
FIG. 2 shows the concentration dependence of cleavage of TcdB cysteine protease domain in the presence of activator compound (7) (empty circles), its PEG2000 analogue (empty triangles), and its methyl analogue (black squares).

The compound to be tested was added to the His-tagged cysteine protease domain of *C. difficile* toxin B (same sequence as given above) in presence of 10 mM Ca$^{2+}$ in 100 mM Tris pH 7.4 and incubated for 24 h at 37° C., with aliquots removed at regular intervals. Cleaved protein fragments were separated, visualized and analyzed as indicated above. The results of this assay for IP6 and compound (7) are shown in FIG. 1B. They demonstrate that the extent of cleavage after 4 h is 5-fold higher with (7) than with IP6.

4. Synthesis of Compound (5a)

Figure 5:
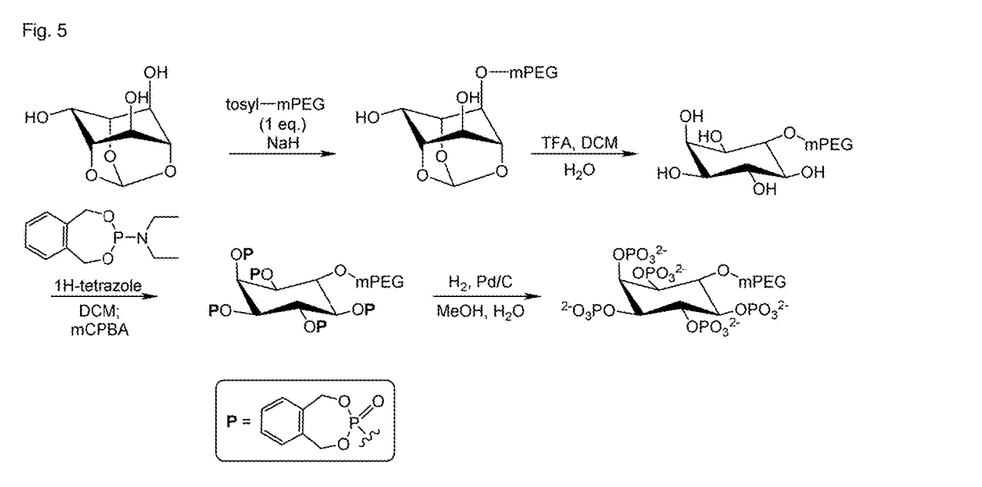
FIG. 5 shows the synthesis scheme of compound (5a).

The synthesis followed the sequence depicted in FIG. 5. The known myo-inositol orthoformate can be mono alkylated with a commercial PEG tosylate in the presence of a strong based such as sodium hydride in DMF. The reaction mixture is then quenched with water and extracted with dichloromethane. The organic layer is dried and concentrated under reduced pressure. The product can be deprotected directly in the presence of TFA in a water and dichloromethane mixture. The crude reaction mixture is evaporated and purified by silica gel chromatography. Phosphorylation of the free hydroxyl groups is done under standard conditions using a phosphoramidite reagent followed by oxidation with meta-chloroperbenzioc acid. The product can be purified by normal or reverse phase chromatography. The final deprotection is performed with palladium on activated carbon under an atmosphere of hydrogen in a mixture of water and methanol. After neutralization of the acidic reaction mixture, the final product can be purified by size-exclusion chromatography or reverse phase chromatography.

5. Synthesis of Compound (6a)

Figure 6:
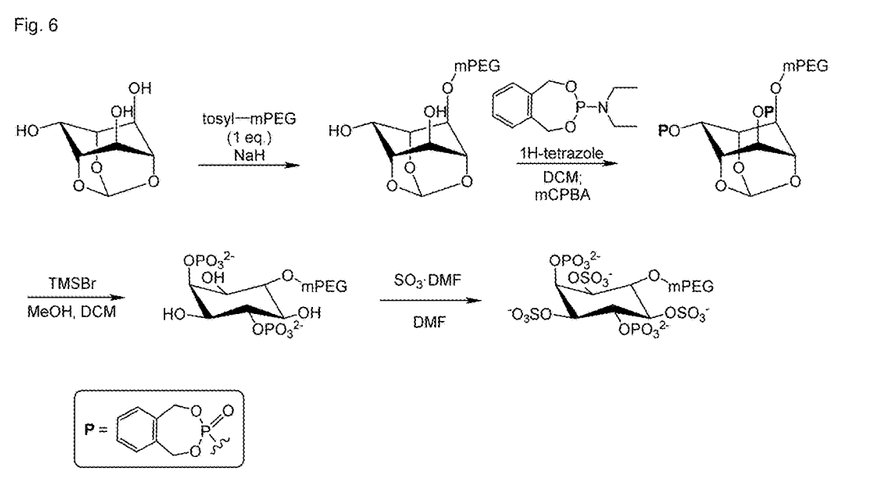
FIG. 6 shows the synthesis scheme of compound (6a).

The synthesis followed the sequence depicted in FIG. 6. The known myo-inositol orthoformate can be mono alkylated with a commercial PEG tosylate in the presence of a strong based such as sodium hydride in DMF. The reaction mixture is then quenched with water and extracted with dichloromethane. The organic layer is dried and concentrated under reduced pressure. The product can be purified by silica gel chromatography. Phosphorylation of the free hydroxyl groups is done under standard conditions using a phosphoramidite reagent followed by oxidation with meta-chloroperbenzioc acid. The product can be purified by normal or reverse phase chromatography. The orthoester and phosphate groups are then deprotected concomitantly using excess bromotrimethylsilane in a mixture of methanol and dichloromethane. The product can be purified by precipitation or reverse phase chromatography. Sulfation of the free hydroxyl group is performed by suspending the product in dry DMF and reacting with excess sulfur trioxide-DMF complex. The reaction is then quenched with water and neutralized. The final product can be precipitated out of the reaction mixture by adding methanol and purified by size-exclusion chromatography or reverse phase chromatography.

6. Calcification Assay

The inventors performed an in vitro assay that measures the propensity for calcification of human serum and has been clinically validated as a predictor of all-cause mortality in CKD patients and renal transplant recipients (as described in Pasch, Journal of the American Society of Nephrology 23, 1744-1752, 2012). The experiment was carried out by mixing a calcium solution, human pooled serum, the test compound at the final concentration indicated and a phosphate solution, and the transition time of primary to secondary calciprotein particles (CPPs) was measured at 37° C. using a nephelometer for up to 600 minutes (FIG. 1). The data shows that the compound 2-IP5-PEG is far more active than all other compounds in this assay. This result suggests a key role of the polymer moiety in preventing the transition of primary to secondary CPPs and in reducing the propensity for calcification of human serum.

We claim:

1. A compound described by a general formula (1)

(1)

wherein $R^1$ is a solubility function $R^2$ selected from the group consisting of a polyethylene glycol and a polyglycerol, and each X independently of any other X is selected from $OPO_3^{2-}$, $OPSO_2^{2-}$, or $OSO_3^-$.

2. The compound according to claim 1, wherein $R^1$ is a polyethylene glycol.

3. The compound according to claim 2, wherein said polyethylene glycol is described by a formula ($R^3$—(O—$CH_2$—$CH_2$)$_n$—) with $R^3$ being hydrogen, methyl or ethyl, and n having a value from 3 to 200.

4. The compound according to claim 2, wherein said polyethylene glycol is described by a formula ($R^3$—(O—$CH_2$—$CH_2$)$_n$—) with $R^3$ being hydrogen, methyl or ethyl, and n having a value selected from 3 to 200, 3 to 20, 10 to 30 and 9 to 45.

5. The compound according to claim 2, wherein said polyethylene glycol is described by a formula ($R^3$—(O—$CH_2$—$CH_2$)$_n$—) with $R^3$ being hydrogen, methyl or ethyl, and n having a value of 7, 9, 11 or 45.

6. The compound according to claim 2 described by a general formula (2a), or (3a)

(2a)

(3a)

(±)

wherein X and $R^1$ have the meaning outlined above.

7. The compound according to claim 2 described by a general formula (2b) or (3b)

(2b)

-continued (3b)

wherein X and R1 have the meaning outlined above.

8. The compound according to claim 2 described by a general formula (4a) or (4b)

(4a)

(4b)

wherein $R^1$ has the meaning outlined above.

9. The compound according to claim 2 described by a general formula (5a) or (5b)

(5a)

(5b)

wherein $R^1$ has the meaning outlined above.

10. The compound according to claim 2 described by a general formula (6a) or (6b)

(6a)

(6b)

wherein $R^1$ has the meaning outlined above.

11. The compound according to claim 2, wherein said polyethylene glycol is $CH_3(OCH_2—CH_2)_9—O—$ or $CH_3(OCH_2—CH_2)_{45}—O—$.

12. The compound according to claim 2, wherein said polyethylene glycol is $CH_3(OCH_2—CH_2)_7—O—$ or $CH_3(OCH_2—CH_2)_{11}—O—$.

13. The compound according to claim 2 described by formula (7)

(7)

14. A compound described by a general formula (1)

(1)

wherein $R^1$ is a polyethylene glycol, each X independently of any other X is selected from $OPO_3^{2-}$, $OPSO_2^{2-}$, or $OSO_3^-$, and wherein said polyethylene glycol is described by a formula $(R^3—(O—CH_2—CH_2)_2—)$ with $R^3$ being hydrogen, methyl or ethyl.

15. The compound according to claim 14 described by a general formula (2a), or (3a)

(2a)

(3a)

wherein X and $R^1$ have the meaning outlined above.

16. The compound according to claim 14 described by a general formula (2b) or (3b)

(2b)

(3b) (±)

wherein X and R1 have the meaning outlined above.

17. The compound according to claim 14 described by a general formula (4a) or (4b)

(4a)

(4b)

wherein $R^1$ has the meaning outlined above.

18. The compound according to claim 14 described by a general formula (5a) or (5b)

(5a) (±)

(5b) (±)

wherein $R^1$ has the meaning outlined above.

19. The compound according to claim 14 described by a general formula (6a) or (6b)

(6a) (±)

(6b) (±)

wherein $R^1$ has the meaning outlined above.

* * * * *